United States Patent [19]

Kalopissis et al.

[11] 4,008,043
[45] Feb. 15, 1977

[54] DIPHENYLAMINES FOR DYEING KERATINIC FIBERS

[75] Inventors: Gregoire Kalopissis, Neuilly-sur-Seine; Andree Bugaut, Boulogne-sur-Seine; Francoise Estradier, Paris, all of France

[73] Assignee: L'Oreal, Paris, France

[22] Filed: Feb. 21, 1975

[21] Appl. No.: 551,627

[30] Foreign Application Priority Data

Feb. 22, 1974 Luxembourg .................... 69457

[52] U.S. Cl. .................................. 8/10.2; 8/10; 8/10.1; 8/11; 8/32; 260/471 C; 260/553 A; 260/559 A; 260/562 N; 260/570.5 P; 260/571; 260/573

[51] Int. Cl.² ............................................ A61K 7/13

[58] Field of Search ........ 260/570.5 P, 571, 471 C, 260/559 A, 562 N, 573; 8/10.1, 10, 10.2, 11, 32

[56] References Cited

FOREIGN PATENTS OR APPLICATIONS 149,676 4/1903 Germany .............................. 8/10.2
209,121 4/1908 Germany .............................. 8/10.2

*Primary Examiner*—Albert T. Meyers
*Assistant Examiner*—Vera C. Clarke
*Attorney, Agent, or Firm*—Cushman, Darby & Cushman

[57] ABSTRACT

Diphenylamine of the formula:

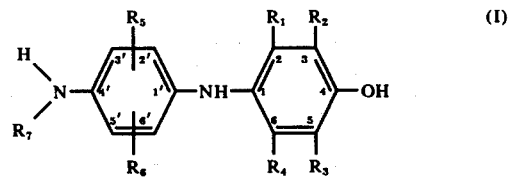

wherein $R_1$ and $R_4$ each independently represent a member selected from the group consisting of hydrogen, halogen, lower alkyl having 1–6 carbon atoms, lower alkoxy having 1–6 carbon atoms, amino, N-lower alkyl amino wherein the alkyl moiety has 1–6 carbon atoms, N-lower hydroxy alkyl amino wherein the alkyl moiety has 1–6 carbon atoms, N-lower carbamylalkyl amino wherein the alkyl moiety has 1–6 carbon atoms, acylamino, wherein the acyl moiety has 2–7 carbon atoms, ureido and carbalkoxyamino wherein the alkoxy moiety has 1–6 carbon atoms;

$R_2$ and $R_3$ each independently represent a member selected from the group consisting of hydrogen, halogen, lower alkyl having 1–6 carbon atoms, lower alkoxy having 1–6 carbon atoms, acylamino wherein the acyl moiety has 2–7 carbon atoms and ureido;

$R_5$ and $R_6$ each independently represent a member selected from the group consisting of hydrogen, halogen, lower alkyl having 1–6 carbon atoms and lower alkoxy having 1–6 carbon atoms with the proviso that when both $R_5$ and $R_6$ are other than hydrogen at least one of $R_5$ and $R_6$ occupies a position meta to $-NHR_7$; and $R_7$ represents a member selected from the group consisting of alkyl having 1–6 carbon atoms, hydroxy alkyl having 1–6 carbon atoms, amino alkyl having 1–6 carbon atoms, acylamino alkyl wherein the acyl moiety has 2–7 carbon atoms and the alkyl moiety has 1–6 carbon atoms, mesylamino alkyl having 1–6 carbon atoms, carbamyl alkyl having 1–6 carbon atoms, sulfo alkyl having 1–6 carbon atoms, piperidino alkyl having 1–6 carbon atoms, morpholino alkyl having 1–6 carbon atoms, mono alkyl amino alkyl wherein each alkyl moiety has 1–6 carbon atoms, dialkyl amino alkyl wherein each alkyl moiety has 1–6 carbon atoms.

The said diphenylamine is usefully employed in a dye composition for dyeing keratinic fibers.

21 Claims, No Drawings

DIPHENYLAMINES FOR DYEING KERATINIC FIBERS

The present invention relates to diphenylamines or N-alkyl leuco indoanilines monosubstituted in the 4' position, to their preparation and to their use for dyeing keratinic fibers, and in particular living human hair.

A currently utilized technique for dyeing keratinic fibers, and especially living human hair, comprises applying to the hair, in the presence of an oxidizing agent added at the moment of use (generally hydrogen peroxide), a dye composition comprising a mixture in an appropriate cosmetic support, of compounds belonging to one or the other of the two following classes.

The first class of compounds, generally called "oxidation bases" is principally constituted by paraphenylenediamines or paraaminophenols which, on oxidation, produce para benzoquinonediimines or parabenzoquinonemonoimines.

The second class of compounds, generally called "couplers" include, especially, metaaminophenols, metaacetylaminophenols, metadiamines and metadiphenols. These compounds, which when reacted with benzoquinone mono- or di-imines produce dyes which, depending upon their structure, are called indophenols, indoanilines or indamines.

These dyes, which provide a range of shades of exceptional richness, importantly are characterized by the luminosity and the richness in glints of dyeings or colorations they impart to the fibers dyed therewith.

However, when a complex dye composition is employed, i.e. a composition which includes several bases and several couplers, it is very difficult to foresee in the final shade the contribution of each possible couple of oxidation base and coupler. In other words, on the one hand, it is very difficult at the outset to predict with any exactitude the final shade that will be attained and, on the other hand, for a given dye composition it is not often easy to be assured of a perfectly reproducible result. These difficulties are increased by the fact that different secondary reactions can modify the final shade, such secondary reactions including, for instance, formation of Bandrowsky base type compounds starting with oxidation bases; recondensation of a molecule of an oxidation base on certain indophenols or on certain indoanilines or indamines; and formation of quinones and the like.

Heretofore it has also been proposed to use in the dyeing of hair some indoanilines which are well defined compounds and which impart to the hair essentially perfectly reproducible shades.

However, some inconvenience has been experienced in the use of these compounds since they possess only a slight affinity for keratinic fibers under conventional conditions for dyeing hair.

The present invention relates to leuco derivatives of indoanilines which are colorless compounds and which, when applied in an aqueous solution to fibers to be dyed, are oxidized at the interior of the keratinic fibers so as to give the corresponding indoanilines. These resulting indoanilines are the colored compounds which are directly responsible for the dyeing of the fibers. The colorations thus obtained exhibit stability and intensity of coloration qualities which are greater than those of dyeings effected by the direct application of indoanilines, because of the enhanced solubility and better keratinic fiber penetration characteristics of the compounds of the present invention.

The oxidation of leuco derivatives of the present invention to indoanilines can be effected by the oxygen in air or by the use of an oxidizing agent incorporated into the dye composition at the moment of use. Representative oxidizing agents include hydrogen peroxide, urea peroxide and ammonium persulfate.

While the use of the leuco derivatives of indoanilines for dyeing hair has already been proposed, the present invention enlarges the family of such leuco derivatives. Thus the leuco derivatives of indoaninlines or diphenylamines of the present invention have the formula

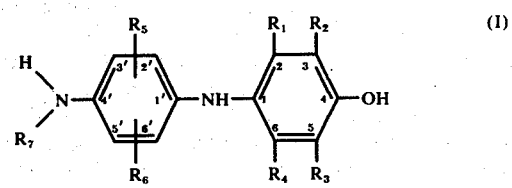

(I)

wherein $R_1$ and $R_4$ each independently represent a member selected from the group consisting of hydrogen, halogen, lower alkyl, lower alkoxy, amino, N-lower alkyl amino, N-lower hydroxyalkyl amino, N-lower carbamylalkyl amino, acylamino, ureido and carbalkoxyamino, $R_2$ and $R_3$ each independently represent a member selected from the group consisting of hydrogen, halogen, lower alkyl, lower alkoxy, acylamino and ureido, $R_5$ and $R_6$ each independently represent a member selected from the group consisting of hydrogen, halogen, lower alkyl and lower alkoxy and can occupy any two free positions on the phenylene ring with the proviso however that when they are both other than hydrogen, at least one of $R_5$ and $R_6$ occupies a position meta relative to the $-NHR_7$ group, i.e. it occupies position 2' or 6'; and $R_7$ represents a member selected from the group consisting of lower alkyl, lower hydroxyalkyl, lower amino alkyl, lower acylaminoalkyl, lower mesylamino alkyl, lower carbamylalkyl, lower sulfoalkyl, lower piperidinoalkyl, lower morpholino alkyl, lower monoalkyl lower aminoalkyl and lower dialkyl lower aminoalkyl.

The above lower alkyl group contains from 1 to 6 and preferably 1 to 4 carbon atoms and the above acyl group contains 2–7 carbon atoms.

The present invention also relates to diphenylamines of formula (I) in the form of their salts, such as, for instance, the hydrochlorides, hydrobromides, sulfates and phosphates thereof.

The diphenylamines of formula (I) are the leuco derivatives of indoanilines of the formula (II)

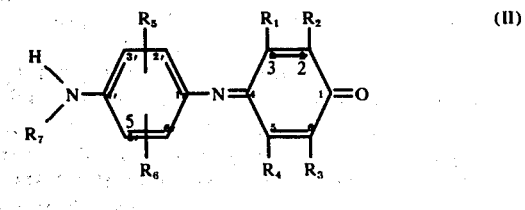

(II)

wherein $R_1$ to $R_7$ have the meanings given above, and can be obtained by the reduction of these indoanilines, preferably by catalytic hydrogenation of the same in the presence of a palladium on carbon catalyst. Alternatively, these indoanilines can be reduced using an alkaline hydrosulfite, preferably sodium or ammonium hydrosulfite, or using an alkaline sulfide, preferably ammonium sulfide.

The diphenylamines of the present invention are usefully employed to dye keratinic fibers and, in particular, living human hair. These diphenylamines, when applied to hair in an aqueous or hydroalcoholic solution, at a concentration ranging between 0.002 to 3 weight percent thereof and preferably between 0.1 to 1 weight percent, provide, after oxidation either with air or by another oxidizing agent such as hydrogen peroxide, urea peroxide or ammonium persulfate, a range of shades which are very rich in the area of pinks to violets, blues and greens. Additionally, the diphenylamines of the present invention provide some very luminous grays and beiges which are rich in glints. The dyeings thus obtained are characterized by richness in glints and their pearly or metallic aspect.

The present invention also relates to a dye composition for keratinic fibers and in particular living human hair, comprising an aqueous or hydroalcoholic solution, and preferably hydroethanolic or hydroisopropanolic solution, containing at least one compound of formula (I).

The dye composition can also include a salt of the diphenylamines of formula (I) and in particular the hydrochloride, hydrobromide, sulfate or phosphate thereof.

The dye composition according to the present invention can include as the active dyeing agent only the compounds of formula (I). However, they can also include other known leuco derivatives of indoanilines, indamines or indophenols, or even oxidation dyes such as ortho- or para-phenylenediamines or ortho- or para-aminophenols, as well as couplers such as metadiamines, metadiphenols, metaaminophenols, metaacetylaminophenols or even direct dyes such as nitrobenzene dyes, azo dyes or anthraquinone dyes, indoanilines, indamines and/or indophenols.

The compositions according to the present invention are generally provided in the form of an aqueous or hydroalcoholic solution containing one or more compounds of formula (I), in admixture or not with other dyes. They can, however, also include thickening agents and be provided in the form of a cream or gel.

Representative thickening agents that can be incorporated into the dye composition of the present invention include cellulose derivatives such as methyl cellulose, hydroxyethyl cellulose, carboxymethyl cellulose or acrylic polymers such as the sodium salt of polyacrylic acid or carboxyvinyl polymers.

The dye compositions can contain as solvents, water, lower alkanols for example ethanol or isopropanol, polyalcohols such as glycols, for example, ethylene glycol, propylene glycol, butyl glycol, diethyleneglycol and the monomethyl ether of diethylene glycol.

The dye composition according to the present invention can also include other components generally employed in cosmetics, such as sequesterants, including ethylene diamine tetra acetic acid and salts thereof; wetting agents including oxyethylenated alkyl phenols, oxyethylenated fatty acids, oxyethylenated fatty alcohols, sulfates and sulfonates of fatty alcohols optionally oxyethylenated; dispersing agents such as the diethanolamides of fatty acids of copra; swelling agents; penetrating agents; emollients; polymers and/or perfumes. The composition of the present invention can also be packaged in aerosol containers together with an aerosol propellant.

Representative aerosol propellants usefully employed in compositions according to the present invention include nitrogen, nitrous oxide, volatile hydrocarbons such as butane, isobutane or propane, or preferably fluorinated hydrocarbons (sold under the name of Freon by Dupont) such as dichlorodifluoromethane, 1,1-difluoromethane, 1,2-dichloro-1,1,2,2-tetrafluoroethane and 1-chloro-1,1-difluoromethane. Mixtures of two or more hydrocarbons or fluorinated hydrocarbons can also be used.

The pH of the compositions of the present invention can vary widely and generally it ranges between about 5.5 to 12 and preferably between about 6 and 11.

The pH of the composition can be adjusted with the aid of an alkalizing agent such as, for example, ammonia, mono-, di- or tri-ethanolamine, di- or tri-sodium phosphate, sodium carbonate or potassium carbonate, or with the aid of an acidifying agent such as, for example, acetic acid, lactic acid, phosphoric acid or citric acid.

The dyeing of keratinic fibers and, in particular, living human hair, with the use of the dye compositions of the present invention, is carried out in a conventional manner by applying the said composition to the fibers to be dyed, permitting said composition to remain in contact with the fibers for a period of time ranging from about 5 to 30 minutes, rinsing and optionally washing the fibers and then drying the fibers. Prior to applying the said composition to the fibers, there can be added to said composition an oxidizing agent such as 25-100 percent by volume of hydrogen peroxide, generally 6% (20 volumes), or 0.1 to 15% by weight of an oxidizing agent such as urea peroxide or ammonium persulfate.

The compositions according to the present invention, when present in the form of a hydroalcoholic solution, can also include a cosmetic resin, so as to provide a colored hair setting lotion which can be applied to wet or moist hair before setting.

Representative cosmetic resins that can be used in the hair setting lotion composition of the present invention include such film-forming polymers as polyvinylpyrrolidone; copolymers of vinylpyrrolidone and vinyl acetate; copolymers of vinyl acetate and an unsaturated carboxylic acid such as crotonic acid; copolymers resulting from the copolymerization of vinyl acetate, crotonic acid and an acrylic or methacrylic ester; copolymers resulting from the copolymerization of vinyl acetate and a vinyl alkyl ether; copolymers resulting from the copolymerization of vinyl acetate,, crotonic acid and a vinyl ester of a long carbon chain acid or even of an allyl or methallyl ester of a long carbon chain acid; copolymers resulting from the copolymerization of an ester derived from an unsaturated alcohol and a short carbon chain acid, of an unsaturated short carbon chain acid and of at least one ester derived from a short carbon chain saturated alcohol and an unsaturated acid; and copolymers resulting from the copolymerizaton of at least one unsaturated ester and at least one unsaturated acid.

Representative preferred cosmetic resins include polyvinylpyrrolidone having a molecular weight ranging between about 10,000 to 360,000; copolymers of 10% crotonic acid and 90% vinyl acetate having a molecular weight ranging between about 10,000 to 70,000; copolymers of vinylpyrrolidone and vinyl acetate having a molecular weight ranging between about 30,000 to 200,000 wherein the ratio of VP to VA ranges between 30:70 to 70:30; copolymers of maleic anhydride and methylvinyl ether in a 1 to 1 molar ratio, having a specific viscosity, measured at 25° C and at a concentration of 1 g in 100 ml of methyl ethyl ketone ranging between about 0.1 and 3.5; the monoethyl, monoisopropyl and monobutyl esters of said maleic anhydride methyl vinyl ether copolymers; copolymers of maleic anhydride and vinylbutyl ether in a 1 to 1 molar ratio; terpolymers of methyl methacrylate (15–25%) stearyl methacrylate (18–28%) and dimethylaminoethyl methacrylate (52–62%); and terpolymers of vinyl acetate (75–85%), allyl stearate (10–20%) and allyloxy-acetic acid (3–10%); the viscosity of which, measured at the boiling point of ether and at a concentration of 5% in dimethylformamide, ranges between about 4.4 and 5 centipoises.

These cosmetic film-forming resins are used generally in an amount between said 1–3 percent by weight of the total hair setting lotion composition.

The alcohols generally employed in the production of the hair setting lotion compositions of the present invention are low molecular weight alcohols, preferably ethanol or isopropanol. These alcohols are used in an amount of about 20 to 70 weight percent of the total composition.

The hair setting lotion composition of the present invention can be utilized in a conventional manner by applying the same to wet or moist hair, previously washed and rinsed, followed by rolling the hair upon curlers and drying the hair.

The preparation of benzoquinoneimines used as initial reactants for the preparation of the diphenylamines takes place by condensing a compound of formula (III), below, in which Z is NO or $NH_2$ and $R_5$, $R_6$ and $R_7$ have the meanings given above, or a salt thereof, on a phenolic compound of formula IV, below, wherein $R_1$, $R_2$, $R_3$ and $R_4$ have the meanings given above, or a salt thereof.

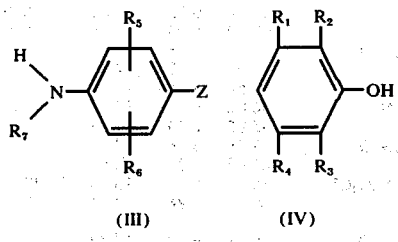

(III)　　(IV)

When Z represents $-NH_2$, the condensation is carried out in an aqueous, hydroalcoholic or hydroacetonic medium at an alkaline pH generally greater than 8, in the presence of an oxidizing agent, for example, ammonium persulfate, potassium ferricyanide and hydrogen peroxide, and at a temperature generally ranging between about 0° to 25° C. The alkaline pH is obtained by means of ammonia or an alkaline carbonate such as sodium carbonate.

When Z represents $-NO$, the condensation is carried out generally at a temperature of about 50° C, in a hydroethanolic medium which is neutral or has been made alkaline by the addition thereto of a dilute sodium hydroxide solution.

The preparation of the diphenylamines of the present invention can advantageously be effected in accordance with the following operation.

To a solution of sodium hydrosulfite in 1N sodium hydroxide to which has been added ethanol and which is maintained at a temperature ranging between about 10° to 40° C, there is added, little by little and with agitation, the benzoquinoneimine in the form of a suspension or a partial solution or a complete solution, in ethanol. The agitation of the resulting mixture is continued and when the reaction is terminated, the reaction medium is filtered to remove any insolubles if such are formed. The reaction medium, cooled to 0° C, is neutralized by adding solid carbon dioxide or acetic acid in an amount sufficient to precipitate the desired leuco derivative. The precipitate is recovered by filtering the reaction medium and is washed with water eventually saturated with carbonic gas. If necessary, the leuco derivative can be recrystallized in a mixture of dimethyl formamide and water and then dried under a vacuum.

The diphenylamines in which $R_1$ or $R_4$ represents an amino group can be prepared starting with benzoquinoneimine having an acetyl-amino group in the indicated position. On deacetylation the benzoquinoneimine corresponding to the diphenylamine is formed, which benzoquinoneimine is then reduced as indicated above.

The following procedures which illustrate the preparation of 3-methoxy-4-hydroxy-6-amino-4'-N-methylamino diphenylamine, indicated below as Example 49, are representative of the method to prepare diphenylamines of the present invention wherein $R_1$ or $R_4$ represents an amino group.

In a first stage, carried out at 0° C, as described above, the dihydrochloride of N-methyl paraphenylene diamine is condensed on 2-methoxy-5-acetylaminophenol, in a hydroacetonic medium and in the presence of ammonium persulfate. The molar ratio of the said phenolic compound to aniline compound is 1:1 and the molar ratio of the said oxidizing agent to the phenolic compound is 2:1. There is obtained N-[(4'-methylamino) phenyl]-2-methoxy-5-acetylamino benzoquinoneimine having a melting point of 207° C.

| | C% | H% | N% |
|---|---|---|---|
| Calculated for $C_{16}H_{17}N_3O_3$ | 64.21 | 5.69 | 14.04 |
| Found | 63.97 | 5.91 | 14.15 |

In a second stage, 0.005 mole of N-[(4'-methylamino) phenyl]-2-methoxy-5-acetylamino benzoquinoneimine in 50 cc of a normal sodium hydroxide solution to which has been added 20 cc of ethanol is agitated at ambient temperature. The said benzoquinoneimine is completely de-acetylated and there are recovered by filtration 1.1 g of N-[(4'-methylamino)phenyl]-2-methoxy-5-amino benzoquinoneimine which, after recrystallization in a mixture of dimethylformamide and water is dried under a vacuum and has the characteristics indicated in Example 49 of Table A below.

In a third stage, the N-[(4'-methylamino)phenyl]-2-methoxy-5-amino benzoquinoneimine is reduced under the conditions appearing in Example 49 of Table II, below, to form 3-methoxy-4-hydroxy-6-amino-4'-N-methylamino diphenylamine having the characteristics given in Example 49 of Table I, below.

The characteristics of the benzoquinoneimine initial reactants are given in Table A, infra, wherein Column I indicates the number of the compound; Column II, its chemical name; Column III, the empirical formula of said compound; Column IV, the melting point of the compound and Column V the elemental analysis of the compound with percentages of carbon, hydrogen, nitrogen and optionally chlorine and sulfur. For the indicated percentages, the first number indicated represents the value calculated for the empirical formula given whereas the second and third numbers represent the value found by analysis.

In Table B are listed the operating conditions for preparing the benzoquinoneimines and the various columns of Table B indicate the number of the compound prepared, the names of the initial reactants (anilines and phenols), the mole ratio of said phenol to said aniline, the nature of the reaction medium, the nature of the oxidizing agent, the mole ratio of oxidizing agent to phenolic compound and the temperature of the reaction.

TABLE A

| I | II | III | IV | V | | | | |
|---|---|---|---|---|---|---|---|---|
| | | | | | | Analyses | | |
| Ex. No. | BENZOQUINONEIMINE | MP (° C) | Empirical Formula | C | H | N | Cl | S |
| 1 | N-[(4'-β-hydroxyethylamino-3'-methyl)-phenyl]-2-methyl 5-acetylamino benzoquinoneimine | 242 | $C_{18}H_{21}N_3O_3$ | 66.03<br>65.85<br>65.87 | 6.47<br>6.65<br>6.44 | 12.84<br>12.93<br>13.06 | | |
| 2 | N-[(4'-β-acetylaminoethylamino-3'-methoxy)-phenyl]-2,6-dimethyl-5-amino benzoquinoneimine | 183 | $C_{19}H_{24}N_4O_3$ | 64.02<br>63.87<br>63.74 | 6.79<br>6.58<br>6.70 | 15.72<br>15.51<br>15.20 | | |
| 3 | N-[(4'-β-mesylamino ethylamino-3'-chloro) phenyl]-2-methyl-5-acetylamino benzoquinoneimine | 244 | $C_{18}H_{21}N_4O_4S\ Cl$ | 50.88<br>50.71<br>50.77 | 4.98<br>5.20<br>5.20 | 13.18<br>13.36<br>13.42 | | 7.54<br>7.26<br>7.38 |
| 4 | N-[(4'-ethylamino-2'methyl)phenyl]-3-ureido benzoquinoneimine | 212 | $C_{16}H_{18}N_4O_2$ | 64.41<br>64.29<br>64.58 | 6.08<br>6.25<br>6.09 | 18.78<br>18.47<br>18.62 | | |
| 5 | N-[(4'-β-mesylaminoethylamino-3'-methyl) phenyl]-2,6-dimethyl-5-acetylamino benzoquinoneimine | 148 | $C_{20}H_{26}N_4O_4S$ | 57.40<br>57.52<br>57.23 | 6.26<br>6.24<br>6.27 | 13.39<br>13.53<br>13.45 | | 7.64<br>7.66<br>7.46 |
| 6 | N-[(4'-ethylamino-3'-methyl)phenyl]-2,6-dimethyl-3-amino benzoquinoneimine | 147 | $C_{17}H_{21}N_3O$ | 72.05<br>71.78<br>71.67 | 7.47<br>7.42<br>7.53 | 14.83<br>15.04<br>14.65 | | |
| 7 | N-[(4'-ethylamino)phenyl]2-methyl-5-carbamylmethylamino benzoquinoneimine | 225 | $C_{17}H_{20}N_4O_2$ | 65.36<br>65.06<br>65.08 | 6.45<br>6.59<br>6.64 | 17.94<br>18.16<br>18.04 | | |
| 8 | N-[(4'-ethylamino)phenyl]2-methyl-5-acetylamino benzoquinoneimine | 100 | $C_{17}H_{19}N_3O_2$ | 68.66<br>68.12<br>68.41 | 6.44<br>6.44<br>6.66 | 14.13<br>13.98<br>13.94 | | |
| 9 | N-[(4'-methylamino)phenyl]2,6-dimethyl-3-acetylamino benzoquinoneimine | 158 | $C_{17}H_{19}N_3O_2$ | 68.66<br>68.29<br>68.32 | 6.44<br>6.57<br>6.58 | 14.13<br>14.25<br>14.34 | | |
| 10 | N-[(4'-methylamino-3'-methoxy)phenyl] 2,6-dimethyl benzoquinoneimine | 156 | $C_{16}H_{18}N_2O_2$ | 71.09<br>70.86<br>70.79 | 6.71<br>6.83<br>6.76 | 10.36<br>10.42<br>10.49 | | |
| 11 | N-[(4'-β-hydroxyethylamino-3'-chloro) phenyl]-3-chloro-6-acetylamino benzoquinoneimine | 144 | $C_{16}H_{15}N_3O_3Cl_2$ | 52.19<br>52.05<br>51.93 | 4.10<br>4.42<br>4.38 | 11.41<br>11.52<br>11.36 | 19.26<br>19.16<br>19.23 | |
| 12 | N-[(4'-ethylamino-3'-chloro)phenyl] 2-methyl-5-acetylamino benzoquinoneimine | 144 | $C_{17}H_{18}N_3O_2Cl$ | 61.53<br>61.57<br>61.28 | 5.46<br>5.61<br>5.51 | 12.66<br>12.53<br>12.86 | 10.68<br>10.79<br>10.65 | |
| 13 | N-[(4'-β-hydroxyethylamino-3'-methoxy) phenyl]-2,6-dimethyl-5-acetylamino benzoquinoneimine | 110 | $C_{19}H_{23}O_4N_3H_2O$ | 60.79<br>60.53<br>60.45 | 6.71<br>6.58<br>6.61 | 11.19<br>11.31<br>11.36 | | |
| 14 | N-[(4'-butylamino-3'-chloro)phenyl] 3-acetylamino benzoquinoneimine | 124 | $C_{18}H_{20}N_3O_2Cl$ | 62.52<br>62.35<br>62.29 | 5.80<br>6.03<br>6.04 | 12.15<br>12.21<br>12.09 | 10.25<br>10.40<br>10.17 | |
| 15 | N-[(4'-β-acetylaminoethylamino-3'-chloro)phenyl]-3-methoxy benzoquinoneimine | 156 | $C_{17}H_{18}N_3O_3Cl$ | 58.70<br>58.41<br>58.56 | 5.18<br>4.97<br>5.04 | 12.08<br>12.20<br>12.17 | | |
| 16 | N-[(4'-ethylamino-3'-methyl)phenyl] 2-methoxy-5-acetylamino benzoquinoneimine | 211 | $C_{18}H_{21}N_3O_3$ | 66.06<br>65.93 | 6.42<br>6.33 | 12.84<br>13.04 | | |
| 17 | N-[ (4'-methylamino-3'-methoxy)phenyl]-2-methyl-5-carbethoxyamino benzoquinoneimine | 179 | $C_{18}H_{21}N_3O_4$ | 62.96<br>63.02 | 6.16<br>6.28 | 12.24<br>12.06 | | |
| 18 | N-[(4'-methylamino-2'-chloro)phenyl]-2-methyl-5-β-hydroxyethylamino benzoquinoneimine | 190 | $C_{16}H_{18}N_3O_2Cl$ | 60.09<br>60.15 | 5.67<br>5.86 | 13.14<br>13.31 | 11.11<br>11.19 | |
| 19 | N-[(4'-methylamino)phenyl]-2-methyl-5-amino benzoquinoneimine | 162 | $C_{14}H_{15}N_3O$ | 69.69<br>68.52<br>68.57 | 6.27<br>6.33<br>6.39 | 17.42<br>17.62<br>17.55 | | |
| 20 | N-[(4'-methylamino-2'-chloro) phenyl[ 2,6-dimethyl-5-acetylamino benzoquinoneimine | 235 | $C_{17}H_{18}ClN_3O_2$ | 61.53<br>61.26 | 5.47<br>5.56 | 12.66<br>12.90 | 10.68<br>10.47 | |
| 21 | N-[(4'-methylamino-2'-methoxy)phenyl] 2,6-dimethyl-5-acetylamino benzoquinoneimine | 249 | $C_{18}H_{21}N_3O_3$ | 66.03<br>65.84 | 6.47<br>6.52 | 12.84<br>12.79 | | |
| 22 | N-[(4'-methylamino-2'-chloro) phenyl] 2-methyl-5-acetylamino benzoquinoneimine | 234 | $C_{16}H_{16}N_3O_2Cl$ | 60.47<br>60.42 | 5.07<br>5.29 | 13.22<br>13.18 | | |
| 23 | N-[(4'-methylamino)phenyl]2,6-dimethyl benzoquinoneimine | 132 | $C_{15}H_{16}N_2O$<br>MW = 240 (a)<br>MW = 239 (b) | 74.97<br>74.68 | 6.71<br>6.91 | 11.66<br>11.44 | | |
| 24 | N-[(4'-methylamino-3'-methyl)phenyl]2,6-dimethyl benzoquinoneimine | 138 | $C_{16}H_{18}N_2O$ | 75.56<br>75.69 | 7.13<br>7.12 | 11.02<br>11.11 | | |
| 25 | N-[(4'-methylamino-3'-chloro)phenyl]2-2,6-dimethyl benzoquinoneimine | 127 | $C_{15}H_{15}ClN_2O$ | 65.58<br>65.41 | 5.50<br>5.60 | 10.19<br>10.24 | 12.90<br>12.90 | |
| 26 | N-[(4'-methylamino-3'-methyl)phenyl]2-methyl-5-amino benzoquinoneimine | 166 | $C_{15}H_{17}N_3O$ | 70.56<br>70.33 | 6.71<br>6.72 | 16.46<br>16.34 | | |

TABLE A-continued

| I | II | III | IV | V | | | | |
|---|---|---|---|---|---|---|---|---|
| | | MP | | | | Analyses | | |
| Ex. No. | BENZOQUINONEIMINE | (° C) | Empirical Formula | C | H | N | Cl | S |
| 27 | N-[(4'-β-hydroxyethylamino-3'-methoxy)phenyl]-2-methyl-5-amino benzoquinoneimine | 150 | $C_{16}H_{19}N_3O_3$ | 63.77<br>63.81<br>64.02 | 6.36<br>6.53<br>6.65 | 13.95<br>14.02<br>14.19 | | |
| 28 | N-[(4'-methylamino-3'-methyl)phenyl] 2,6-dimethyl-5-amino benzoquinoneimine | 152 | $C_{16}H_{19}N_3O$ | 71.34<br>71.20 | 7.11<br>7.01 | 15.60<br>15.73 | | |
| 29 | N-[(4'-methylamino)phenyl]2,6-dimethyl-3-amino benzoquinoneimine | 166 | $C_{15}H_{17}N_3O$ | 70.56<br>70.75<br>70.41 | 6.71<br>6.67<br>6.68 | 16.46<br>16.49<br>16.52 | | |
| | | | MW = 255 (a)<br>MW = 251 (b) | | | | | |
| 30 | N-[(4'-methylamino-3'-chloro)phenyl] 3-acetylamino benzoquinoneimine | 198 | $C_{15}H_{14}N_3O_2Cl$ | 59.31<br>59.21 | 4.61<br>4.81 | 13.84<br>13.93 | | |
| 31 | N-[(4'-methylamino)phenyl]2-methyl-5-acetylamino benzoquinoneimine | 161 | $C_{16}H_{17}N_3O_2$ | 67.82<br>67.72 | 6.05<br>6.18 | 14.83<br>14.92 | | |
| 32 | N-[(4'-methylamino-3'-methyl)phenyl] 2-methyl-5-acetylamino benzoquinoneimine | 210 | $C_{17}H_{19}N_3O_2$ | 68.66<br>68.64 | 6.44<br>6.49 | 14.13<br>14.28 | | |
| 33 | N-[(4'-ethylamino-3'-methyl)phenyl] 2-methyl-5-acetylamino benzoquinoneimine | 185 | $C_{18}H_{21}N_3O_2$ | 69.45<br>69.20 | 6.75<br>7.00 | 13.50<br>13.74 | | |
| 34 | N-[(4'-β-hydroxyethylamino-3'-chloro)phenyl]3-acetylamino benzoquinoneimine | 178 | $C_{16}H_{16}N_3O_3Cl$ | 57.57<br>57.39 | 4.79<br>4.79 | 12.59<br>12.71 | 10.64<br>10.48 | |
| 35 | N-[(4'-β-hydroxyethylamino-3'-chloro)phenyl] 2-methyl-5-acetylamino benzoquinoneimine | 176 | $C_{17}H_{18}N_3O_3Cl$ | 58.70<br>58.83 | 5.18<br>5.19 | 12.08<br>12.17 | 10.21<br>10.36 | |
| 36 | N-[(4'-methylamino-3'-chloro)phenyl] 2,6-dimethyl-5-acetylamino benzoquinoneimine | 166 | $C_{17}H_{18}ClN_3O_2$ | 61.53<br>61.61 | 5.47<br>5.62 | 12.66<br>12.51 | 10.68<br>10.53 | |
| 37 | N-[(4'-methylamino-3'-methyl)phenyl] 2,6-dimethyl-3-acetylamino benzoquinoneimine | 160 | $C_{18}H_{21}N_3O_2$ | 69.43<br>69.36 | 6.80<br>6.73 | 13.50<br>13.28 | | |
| 38 | N-[(4'-methylamino-3'-chloro)phenyl] 2-methyl-5-acetylamino benzoquinoneimine | 206 | $C_{16}H_{16}ClN_3O_2$ | 60.45<br>60.35 | 5.07<br>5.23 | 13.22<br>13.31 | | |
| 39 | N-[(4'-methylamino-3'-chloro)phenyl] 2,6-dimethyl-3-ureido benzoquinoneimine | 218 | $C_{16}H_{17}N_4O_2Cl$ | 57.74<br>57.77 | 5.11<br>5.45 | 16.84<br>16.90 | | |
| 40 | N-[(4'-methylamino-3'-chloro)phenyl] 3-ureido benzoquinoneimine | 258 | $C_{14}H_{13}N_4O_2Cl$ | 55.17<br>55.14 | 4.27<br>4.56 | 18.39<br>18.64 | 11.66<br>11.57 | |
| 41 | N-[(4'-β-hydroxyethylamino-3'-chloro phenyl] 2,6-dimethyl-3-ureido benzoquinoneimine | 195 | $C_{17}H_{19}N_4O_3Cl$ | 56.30<br>56.41 | 5.24<br>5.34 | 15.42<br>15.33 | 9.79<br>9.81 | |
| 42 | N-[(4'-β-hydroxyethylamino-3'-chloro)phenyl] 3-ureido benzoquinoneimine | >280<br>(decomp.) | $C_{15}H_{15}N_4O_3Cl$ | 53.81<br>53.86 | 4.48<br>4.71 | 16.74<br>16.62 | 10.61<br>10.36 | |
| 43 | N-[(4'-methylamino-3'-chloro)phenyl] 2-methyl-5-ureido benzoquinoneimine | 228 | $C_{15}H_{15}N_4O_2Cl$ | 56.51<br>56.61 | 4.71<br>4.90 | 17.58<br>17.63 | 11.14<br>10.93 | |
| 44 | N-[(4'-β-hydroxyethylamino-3'-chloro)phenyl] 2-methyl-5-ureido benzoquinoneimine | 240 | $C_{16}H_{17}N_4O_3Cl$ | 55.09<br>54.84<br>54.83 | 4.88<br>4.97<br>4.91 | 16.07<br>16.03<br>16.00 | 10.18<br>10.18<br>10.30 | |
| 45 | N-[(4'-methylamino-3'-chloro)phenyl] 2-methyl-5-carbamylmethylamino benzoquinoneimine | 120<br>212 (c) | $C_{16}H_{17}N_4O_2Cl . H_2O$ | 54.78<br>54.67 | 5.46<br>5.16 | 16.26<br>16.53 | 10.11<br>10.13 | |
| 46 | N-[(4'-methylamino)phenyl] 2-methyl 5-carbamylmethylamino benzoquinoneimine H₂O | 228 | $C_{16}H_{18}N_4O_2 . H_2O$ | | | 17.71<br>17.40 | | |
| | | | MW = 298 (a)<br>MW = 304 (b) | | | | | |
| 47 | N-[(4'-methylamino-3'-chloro)phenyl] 2,5-dimethyl benzoquinoneimine | 120 | $C_{15}H_{15}ClN_2O$ | 65.57<br>65.56 | 5.50<br>5.60 | 10.20<br>10.19 | 12.90<br>12.91 | |
| 48 | monohydrate of N-[(4'-methylamino-2'-chloro)phenyl] 2-chloro-5-acetylamino benzoquinoneimine | 258 | $C_{15}H_{13}N_3O_2Cl_2 . H_2O$ | | | 11.79<br>11.94<br>11.88 | 19.94<br>19.58<br>19.57 | |
| 49 | monohydrate of N-[(4'-methylamino)phenyl] 2-methoxy-5-amino benzoquinoneimine | 117 | $C_{14}H_{15}N_3O_2 . H_2O$ | 61.08<br>60.94 | 6.18<br>6.25 | 15.27<br>15.36 | | |

(a) molecular weight calculated
(b) molecular weight determined by potentiometric dosing in acetic acid with perchloric acid
(c) double melting point

TABLE B

| Example No. | ANILINE (Substituted) | PHENOLIC COMPOUND | Molar Ratio of phenol/aniline | Reaction Medium | Oxidizing Agent | Molar Ratio of oxidizing agent to phenol | Temp. (°C) |
|---|---|---|---|---|---|---|---|
| 1 | 2-methyl-4-amino-N-(β-hydroxyethyl) aniline sulfate | 2-methyl-5-acetylamino phenol | 1 : 1 | acetone-water | ammonium persulfate | 2 : 1 | 0 |
| 2 | 2-methoxy-4-amino-N-(β-acetylamino-ethyl) aniline sulfate | 2,6-dimethyl-5-amino phenol hydrochloride | 1 : 1 | water | ammonium persulfate | 1 : 1 | 0 |
| 3 | 2-chloro-4-amino-N-(β-mesylamino-ethyl) aniline sulfate | 2-methyl-5-acetylamino phenol | 1 : 1 | acetone-water ammonium persulfate | 2 : 1 | 0 | |
| 4 | 3-methyl-4-amino-N-ethylaniline dihydrochloride | 3-ureido phenol | 1 : 1 | acetone-water | ammonium persulfate | 1 : 1 | 0 |
| 5 | 2-methyl-4-amino-N-(β-mesylamino-ethyl) aniline sulfate | 2,6-dimethyl-5-acetylamino phenol | 1 : 1 | acetone-water | ammonium persulfate | 1 : 1 | 0 |
| 6 | 2-methyl-4-nitroso-N-ethylaniline | 2,6-dimethyl-3-amino phenol hydrochloride | 1 : 1 | ethanol-water | | | 40 |
| 7 | 4-nitroso-N-ethylaniline | 2-methyl-5-carbamyl- | 1 : 1 | ethanol-water | | | 50 |

TABLE B-continued

| Example No. | ANILINE (Substituted) | PHENOLIC COMPOUND | Molar Ratio of phenol/aniline | Reaction Medium | Oxidizing Agent | Molar Ratio of oxidizing agent to phenol | Temp. (° C) |
|---|---|---|---|---|---|---|---|
| 8 | N-ethyl paraphenylene diamine hydrochloride | 2-methyl-5-acetylamino methylamino phenol | 1 : 1 | acetone-water | ammonium persulfate | 1 : 1 | 0 |
| 9 | N-methyl paraphenylenediamine dihydrochloride | 2,6-dimethyl-3-acetylamino phenol | 1 : 1 | acetone-water | ammonium persulfate | 1 : .1 | 0 |
| 10 | 2-methoxy-4-amino-N-methylaniline sulfate | 2,6-dimethyl phenol | 1 : 1 | acetone-water | ammonium persulfate | 2 : 1 | 0 |
| 11 | 2-chloro-4-amino-N-(β-hydroxyethyl) aniline sulfate | 3-chloro-6-acetyl-amino phenol | 1 : 1 | water-acetone | ammonium persulfate | 1 : 1 | 0 |
| 12 | 2-chloro-4-amino-N-ethylaniline sulfate | 2-methyl-5-acetyl-amino phenol | 1 : 1 | acetone-water | ammonium persulfate | 1 : 1 | 0 |
| 13 | 2-methoxy-4-amino N-(β-hydroxyethyl) aniline sulfate | imethyl-5-acetylamino phenol | 1 : 1 | water-acetone | ammonium persulfate | 1.1 : 1 | 0 |
| 14 | 2-chloro-4-amino N-butylaniline sulfate | 3-acetylamino phenol | 1 : 1 | acetone-water | ammonium persulfate | 1 : 1 | 0 |
| 15 | 2-chloro-4-amino N-(β-acetylamino-ethyl) aniline sulfate | 3-methoxy phenol | 1 : 1 | acetone-water | ammonium persulfate | 2 : 1 | 0 |
| 16 | 2-methyl-4-amino N-ethylaniline sulfate | 2-methoxy-5-acetyl-amino phenol | 1 : 1 | acetone-water | ammonium persulfate | 2 : 1 | 0 |
| 17 | 2-methoxy-4-amino-N-methylaniline sulfate | 2-methyl-5-carbethoxyamino phenol | 1 : 1 | acetone-water | ammonium persulfate | 2 : 1 | 0 |
| 18 | 3-chloro-4-amino-N-methylaniline dihydrochloride | 2-methyl-5-N-β hydroxyethylamino phenol | 1 : 1 | ethanol-water | ammonium persulfate | 1 : 1 | 0 |
| 19 | 4-nitroso-N-methylaniline | 2-methyl-5-amino-phenol | 1 : 1 | ethanol-water | | | 45 |
| 20 | monohydrate of 3-chloro-4-amino-N-methylaniline dihydrochloride | 2,6-dimethyl-5-acetylamino phenol | 1 : 1 | acetone-water | ammonium persulfate | 2 : 1 | 5 |
| 21 | 3-methoxy-4-amino-N-methylaniline dihydrochloride | 2,6-dimethyl-5-acetylamino phenol | 1 : 0.85 | acetone-water | ammonium persulfate | 2 : 1 | 0 |
| 22 | monohydrate of 3-chloro-4-amino-N-methylaniline dihydrochloride | 2-methyl 5-acetylamino phenol | 1 : 0.65 | acetone-water | ammonium persulfate | 2 : 1 | 5 |
| 23 | N-methyl paraphenylene-diamine dihydrochloride | 2,6-dimethyl phenol | 1 : 1 | acetone-water | ammonium persulfate | 2 : 1 | 15 |
| 24 | 2-methyl-4-amino N-methyl-aniline sulfate | 2,6-dimethyl phenol | 1 : 1 | acetone-water | ammonium persulfate | 2 : 1 | 15 |
| 25 | 2-chloro-4-amino-N-methyl-aniline sulfate | 2,6-dimethyl phenol | 1 : 1 | acetone-water | ammonium persulfate | 2 : 1 | 10 |
| 26 | 2-methyl-4-amino-N-methyl-aniline sulfate | 2-methyl-5-amino phenol | 1 : 1 | acetone-water | ammonium persulfate | 2 : 1 | 10 |
| 27 | 2-methoxy-4-amino N-(β-hydroxyethyl) aniline sulfate | 2-methyl-5-amino phenol | 1 : 1 | isopropanol-water | ammonium persulfate | 1 : 1 | 5 |
| 28 | 2-methyl-4-amino-N-methyl-aniline sulfate | 2,6-dimethyl-5-amino phenol hydrochloride | 1 : 1 | acetone-water | ammonium persulfate | 1 : 1 | 5 |
| 29 | N-methyl paraphenylenediamine dihydrochloride | 2,6-dimethyl 3-amino phenol hydrochloride | 1 : 1 | acetone-water | ammonium persulfate | 1 : 1 | 0 |
| 30 | 2-chloro-4-amino-N-methyl-aniline sulfate | 3-acetylamino phenol | 1 : 1 | acetone-water | ammonium persulfate | 2 : 1 | 5 |
| 31 | 4-amino-N-methyl-aniline dihydrochloride | 2-methyl-5-acetylamino phenol | 1 : 1 | acetone-water | ammonium persulfate | 1 : 1 | 0 |
| 32 | 2-methyl-4-amino-N-methyl-aniline sulfate | 2-methyl-5-acetylamino phenol | 1 : 1 | acetone-water | ammonium persulfate | 2 : 1 | 10 |
| 33 | 2-methyl-4-amino N-ethyl-aniline sulfate | 2-methyl-5-acetylamino phenol | 1 : 1 | acetone-water | ammonium persulfate | 2 : 1 | 5 |
| 34 | 2-chloro-4-amino-N(β-hydroxyethyl) aniline sulfate | 3-acetylamino phenol | 1 : 1 | isopropanol-water | ammonium persulfate | 2 : 1 | 0 |
| 35 | 2-chloro-4-amino-N(β-hydroxyethyl) aniline sulfate | 2-methyl-5-acetylamino phenol | 1 : 1 | isopropanol-water | ammonium persulfate | 2 : 1 | 0 |
| 36 | 2-chloro-4-amino N-methyl aniline sulfate | 2,6-dimethyl-5-acetylamino phenol | 1 : 1 | acetone-water | ammonium persulfate | 2 : 1 | 5 |

TABLE B-continued

| Example No. | ANILINE (Substituted) | PHENOLIC COMPOUND | Molar Ratio of phenol/aniline | Reaction Medium | Oxidizing Agent | Molar Ratio of oxidizing agent to phenol | Temp. (°C) |
|---|---|---|---|---|---|---|---|
| 37 | 2-methyl-4-amino N-methyl aniline sulfate | 2,6-dimethyl-3-acetylamino phenol | 1 : 1 | acetone-water | ammonium persulfate | 2 : 1 | 10 |
| 38 | 2-chloro-4-amino N-methyl aniline sulfate | 2-methyl-5-acetylamino phenol | 1 : 1 | acetone-water | ammonium persulfate | 2 : 1 | 10 |
| 39 | 2-chloro-4-amino N-methyl aniline sulfate | 2,6-dimethyl-3-ureido phenol | 1 : 1 | acetone-water | ammonium persulfate | 2 : 1 | 5 |
| 40 | 2-chloro-4-amino-N-methyl aniline sulfate | 3-ureido phenol | 1 : 1 | acetone-water | ammonium persulfate | 2 : 1 | 5 |
| 41 | 2-chloro-4-amino-N-($\beta$-hydroxyethyl) aniline sulfate | 2,6-dimethyl-3-ureido phenol | 1 : 1 | acetone-water | ammonium persulfate | 2 : 1 | 0 |
| 42 | 2-chloro-4-amino N-($\beta$-hydroxyethyl) aniline sulfate | 3-ureido phenol | 1 : 1 | acetone-water | ammonium persulfate | 2 : 1 | |
| 43 | 2-chloro-4-amino-N-methylaniline sulfate | 2-methyl-5-ureido phenol | 1 : 1 | propanol-water | ammonium persulfate | 2 : 1 | 0 |
| 44 | 2-chloro-4-amino N($\beta$-hydroxyethyl) aniline sulfate | 2-methyl-5-ureido phenol | 1 : 1 | isopropanol-water | ammonium persulfate | 2 : 1 | 0 to 5 |
| 45 | 2-chloro-4-amino-N-methylaniline sulfate | 2-methyl-5-carbamyl-methylamino phenol | 1 : 1 | acetone-water | ammonium persulfate | 2 : 1 | 0 |
| 46 | 4-amino N-methylaniline dihydrochloride | 2-methyl-5-carbamyl-methylamino phenol | 1 : 1 | acetone-water | ammonium persulfate | 2 : 1 | 0 |
| 47 | 4-amino-2-chloro N-methylaniline sulfate | 2,5-dimethyl phenol | 1 : 1 | acetone-water | ammonium persulfate | 2 : 1 | 0 to 5 |
| 48 | monohydrate of 3-chloro 4-amino N-methylaniline dihydrochloride | 2-chloro-5-acetylamino phenol | 1 : 1 | acetone-water | ammonium persulfate | 2 : 1 | 10 |

The present invention is illustrated by the following non-limiting examples.

Diphenylamines prepared in accordance with the present invention are listed in Table I in which Column I indicates the number of the compound prepared, which corresponds to the number of the benzoquinoneimine of Tables A and B; Column II gives the chemical name of the diphenylamine; Column III, the melting point of said diphenylamine; Column IV, the empirical formula of said diphenylamine and Column V, the elemental analysis of the diphenylamine with percentages of carbon, hydrogen and nitrogen and optionally chlorine and sulfur. For the indicated percentages, the first number indicated represents the value calculated for the empirical formula given whereas the second and third numbers represent the value found by analysis.

In Table II are listed the operating conditions for the preparation of representative ones of the compounds appearing in Table I. In Table II, Column I indicates the number of the compound prepared; Column II identifies the benzoquinoneimine initial reactant and the quantity employed to produce the diphenylamine; Column III gives the quantity of sodium hydrosulfite employed; Column IV lists the quantity of sodium hydroxide used; Column V indicates the reaction temperature and Column VI gives the quantity of ethanol added (a) to the sodium hydrosulfite solution or (b) to act as a solubilizer for the benzoquinoneimine.

The examples of use involving the dye compositions of the present invention are tabulated in Table III and the examples of use involving hair setting lotion compositions containing a cosmetic film-forming agent are tabulated in Table IV.

In Table III, Column I indicates the number of the example; Column II identifies the diphenylamine dye by the corresponding example number of the same as it appears in Table I and the percentage thereof in the composition; Column III identifies the adjuvants employed and the weight percent thereof; Column IV gives the nature and weight percent of the solvent; Column V lists the nature, quantity and concentration of the oxidizing agent present in the composition; Column VI gives the pH of the composition and Columns VII and VIII indicate, respectively, the nature of the hair to be dyed and the color achieved on dyeing the same.

In Table IV, Column I indicates the number of the Example; Column II identifies the diphenylamine employed by the corresponding example number of the same as it appears in Table I and the percentage thereof in the composition; Column III identifies the chemical name, the molecular weight and the concentration or percentage of the cosmetic film-forming resin used in the composition; Column IV identifies the alcohol and amount thereof employed in the composition; Column V indicates the pH of the composition and Columns VI and VIII identify respectively the nature of the hair treated with the composition and the color achieved with the said composition.

TABLE I

| Ex No. | DIPHENYLAMINE | M.P. (° C) | EMPIRICAL FORMULA | ANALYSIS C% | H% | N% | Cl% | S% |
|---|---|---|---|---|---|---|---|---|
| 1 | 3,3'-dimethyl-4-hydroxy-6-acetylamino-4'-β (hydroxyethyl) amino diphenylamine | 184 | $C_{18}H_{23}N_3O_3$ | 65.63 65.47 65.39 | 7.04 7.12 7.25 | 12.76 12.64 12.59 | | |
| 2 | 3,5-dimethyl-2-amino-4-hydroxy-3'-methoxy-4'-acetylaminoethylamino diphenylamine | 162 | $C_{19}H_{26}N_4O_3$ | 63.66 63.81 | 7.31 7.58 | 15.63 15.75 | | |
| 3 | 3-methyl-4-hydroxy-6-acetylamino-3'-chloro-4'-mesylaminoethylamino diphenylamine | 98 | $C_{18}H_{23}N_4O_4Cl\ S$ | 50.64 50.38 50.42 | 5.43 5.57 5.60 | 13.12 13.22 13.26 | | 7.51 7.56 7.46 |
| 4 | 2-ureido-4-hydroxy-2'-methyl-4'-N-ethylamino diphenylamine | 140 | $C_{16}H_{20}N_4O_2$ | 63.98 63.56 63.50 | 6.71 6.84 6.87 | 18.65 18.54 18.46 | | |
| 5 | 3,3',5-trimethyl-2-acetylamino-4-hydroxy-4'-N-mesylaminoethylamino diphenylamine | 120 | $C_{20}H_{28}N_4O_4S$ | 57.13 56.84 56.98 | 6.71 6.75 6.57 | 13.33 13.32 13.47 | | 7.61 7.83 7.81 |
| 6 | 3,3',5-trimethyl-2-amino-4-hydroxy-4'-N-ethylamino diphenylamine | 136 | $C_{17}H_{23}N_3O$ MW = 285 (a) MW = 289 (b) | 71.54 71.78 71.60 | 8.12 8.06 8.12 | 14.73 14.55 14.75 | | |
| 7 | 3-methyl-4-hydroxy-6-carbamyl-methylamino-4'N-ethylamino diphenylamine | 195 | $C_{17}H_{22}N_4O_2$ MW = 314 (a) MW = 316 (b) | 64.94 64.68 64.77 | 7.05 7.05 7.12 | 17.82 17.63 17.60 | | |
| 8 | 3-methyl-4-hydroxy-6-acetylamino-4'-N-ethylamino diphenylamine | 194 | $C_{17}H_{21}N_3O_2$ MW = 299 (a) MW = 292 (b) | 68.20 68.04 67.96 | 7.07 7.11 7.16 | 14.04 14.12 14.08 | | |
| 9 | 3,5-dimethyl-4-hydroxy-2-acetylamino 4'-N-methylamino diphenylamine | 170 | $C_{17}H_{21}N_3O_2$ | 68.20 68.00 67.98 | 7.07 7.09 7.13 | 14.04 14.04 14.08 | | |
| 10 | 3,5-dimethyl-4-hydroxy-3'-methoxy-4'-N-methylamino diphenylamine | 133 | $C_{16}H_{20}N_2O_2$ MW = 270 (a) MW = 273 (b) | 70.56 70.32 70.28 | 7.40 7.20 7.26 | 10.29 10.26 10.45 | | |
| 11 | monohydrate of 2-chloro-4-hydroxy-5-acetylamino-3'-chloro-4'-N (β-hydroxyethyl) amino diphenylamine | 125 | $C_{16}H_{17}N_3O_2Cl_2 \cdot H_2O$ | 49.50 49.73 49.82 | 4.93 4.96 4.76 | 10.81 10.81 10.91 | 18.30 18.10 18.22 | |
| 12 | 3-methyl-4-hydroxy-6-acetylamino-3'-chloro-4'-N-ethylamino diphenylamine | 206 | $C_{17}H_{20}N_3O_2Cl$ MW = 333.5 (a) MW = 329 (b) | 61.17 60.67 60.76 | 6.04 6.16 6.18 | 12.58 12.27 | 10.62 10.48 10.42 | |
| 13 | monohydrate of 3,5-dimethyl-4-hydroxy-6-acetylamino-3'-methoxy-4'-N-(β-hydroxyethyl) amino diphenylamine | 129 | $C_{19}H_{25}N_3O_4 \cdot H_2O$ MW = 377 (a) MW = 376 (b) | 60.46 60.18 60.33 | 7.21 7.06 7.12 | 11.13 10.98 10.90 | | |
| 14 | 2-acetylamino-4-hydroxy-3'-chloro-4'-N-butylamino diphenylamine | 170 | $C_{18}H_{22}N_3O_2Cl$ MW = 348 MW = 345 (b) | 62.16 61.82 61.78 | 6.38 6.51 6.47 | 12.08 12.04 11.98 | 10.19 10.28 10.23 | |
| 15 | 2-methoxy-4-hydroxy-3'-chloro-4'-acetylaminoethylamino diphenylamine | 160 | $C_{17}H_{20}N_3O_3Cl$ | 58.36 58.29 58.47 | 5.72 5.73 5.68 | 12.01 12.00 11.82 | 10.15 10.24 10.24 | |
| 16 | 3-methoxy-4-hydroxy-6-acetylamino-3'-methyl-4'-N-ethylamino diphenylamine | 163 | $C_{18}H_{23}N_3O_3$ | 65.65 65.45 | 6.99 6.80 | 12.77 12.65 | | |
| 17 | monohydrate of 3-methyl-4-hydroxy-6-carbethoxy amino-3'-methoxy-4'-N-methylamino diphenylamine | 122 | $C_{18}H_{23}N_3O_4 \cdot H_2O$ | 59.50 59.30 | 6.88 6.81 | 11.57 11.82 | | |
| 18 | 3-methyl-4-hydroxy-6-β-hydroxy-ethylamino-2'-chloro-4'-N-methylamino diphenylamine | 152 | $C_{16}H_{20}N_3O_2Cl$ | 59.72 59.62 | 6.22 6.38 | 13.06 13.07 | | |
| 19 | 3-methyl-4-hydroxy-6-amino-4'-N-methylamino diphenylamine | 182 | $C_{14}H_{17}N_3O$ | 69.11 69.16 | 7.04 6.95 | 17.27 17.36 | | |
| 20 | 3,5-dimethyl-4-hydroxy-2-acetylamino-2'-chloro-4'-N-methylamino diphenylamine | 193 | $C_{17}H_{20}N_3O_2Cl$ | | | 12.59 12.77 | 10.64 10.70 | |
| 21 | 3,5-dimethyl-4-hydroxy-2-acetylamino-2'-methoxy-4'-N-methylamino diphenylamine | 210 | $C_{18}H_{23}N_3O_3$ | 65.63 65.50 | 7.04 6.97 | 12.76 12.79 | | |
| 22 | 3-methyl-4-hydroxy-6-acetylamino-2'-chloro-4'-N-methylamino diphenylamine | 210 | $C_{16}H_{18}N_3O_2Cl$ | 60.09 60.05 | 5.63 5.90 | 13.14 12.95 | 11.11 10.94 | |
| 23 | 3,5-dimethyl-4-hydroxy-4'-N-methylamino diphenylamine | 120 | $C_{15}H_{18}N_2O$ | 74.35 74.45 | 7.49 7.38 | 11.56 11.74 | | |
| 24 | dihydrochloride of 3,3',5-trimethyl-4-hydroxy-4'-N-methylamino diphenylamine | 200 (c) | $C_{16}H_{20}N_2O \cdot 2HCl$ | | | 8.51 8.74 | 21.53 21.31 | |
| 25 | 3,5-dimethyl-4-hydroxy-3'-chloro-4'-N-methylamino diphenylamine | 75 | $C_{15}H_{17}N_2O\ Cl$ | 65.09 65.36 | 6.14 6.34 | 10.12 10.28 | 12.84 13.09 | |
| 26 | 3,3'-dimethyl-4-hydroxy-6-amino-4'-N-methylamino diphenylamine | 192 | $C_{15}H_{19}N_3O$ | 70.00 69.80 | 7.44 7.33 | 16.33 16.21 | | |
| 27 | monohydrate of 3-methyl-4-hydroxy-6-amino-4'-N-(β-hydroxyethyl)amino-3'-methoxy diphenylamine | 110 | $C_{16}H_{21}N_3O_3H_2O$ | 59.81 59.87 | 7.10 6.70 | 13.08 13.07 | | |
| 28 | semi-hydrate of 3,3',5-trimethyl-4-hydroxy-2-amino-4'-N-methylamino diphenylamine | 145 | $C_{16}H_{21}N_3O \cdot 0.5H_2O$ | 68.57 68.53 | 8.21 7.84 | 15.00 14.95 | | |
| 29 | 3,5-dimethyl-4-hydroxy-2-amino-4'-N-methylamino diphenylamine | 135 | $C_{15}H_{19}N_3O$ | 70.00 69.70 | 7.44 7.26 | 16.33 16.57 | | |
| 30 | 2-acetylamino-4-hydroxy-3'-chloro-4'-N-methylamino diphenylamine | 182 | $C_{15}H_{16}N_3O_2Cl$ | 58.92 58.99 | 5.24 5.37 | 13.74 13.88 | 11.62 11.48 | |
| 31 | 3-methyl-4-hydroxy-6-acetylamion-4'-N-methyl-amino diphenylamine | 178 | $C_{16}H_{19}N_3O_2$ | 67.34 67.37 | 6.71 6.90 | 14.73 14.70 | | |
| 32 | 3,3'-dimethyl-4-hydroxy-6-acetylamino-4'-N-methylamino diphenylamine | 201 | $C_{17}H_{21}N_3O_2$ | 68.20 68.40 | 7.07 6.99 | 14.04 14.06 | | |
| 33 | 3,3'-dimethyl-4-hydroxy-6-acetylamino-4'-N-ethylamino diphenylamine | 205 | $C_{18}H_{23}N_3O_2$ | 69.01 69.26 | 7.35 7.00 | 13.42 13.58 | | |
| 34 | 2-acetylamino-4-hydroxy-3'-chloro-4'-N (β-hydroxyethyl) amino diphenylamine | 121 | $C_{16}H_{18}N_3O_3Cl$ | 57.22 57.26 | 5.36 5.26 | 12.51 12.40 | | |
| 35 | 3-methyl-4-hydroxy-6-acetylamino-3'-chloro-4'-N-(β-hydroxyethyl)amino diphenylamine | 175 | $C_{17}H_{20}N_3O_3Cl$ | 58.37 58.24 | 5.72 5.96 | 12.02 12.04 | | |
| 36 | 3,5-dimethyl-4-hydroxy-2-acetylamino- | 229 | $C_{17}H_{20}N_3O_2Cl$ | 61.17 | 5.99 | 12.59 | 10.64 | |

TABLE I-continued

| Ex. No. | DIPHENYLAMINE | M.P. (° C) | EMPIRICAL FORMULA | C% | H% | N% | Cl% | S% |
|---|---|---|---|---|---|---|---|---|
| | 3'-chloro-4'-N-methylamino diphenylamine | | | 61.14 | 6.14 | 12.79 | 10.56 | |
| 37 | 3,3'5-trimethyl-4-hydroxy-2-acetylamino-4'-N-methylamino diphenylamine | 220 | $C_{18}H_{23}N_3O_2$ | 68.98 | 7.40 | 13.41 | | |
| | | | | 68.93 | 7.51 | 13.64 | | |
| 38 | 3-methyl-4-hydroxy-6-acetylamino-3'-chloro-4'-N-methylamino diphenylamine | 203 | $C_{16}H_{18}N_3O_2Cl$ | 60.09 | 5.63 | 13.14 | 11.11 | |
| | | | | 60.30 | 5.82 | 13.34 | 10.97 | |
| 39 | 3,5-dimethyl-2-ureido-4-hydroxy-3'-chloro-4'-N-methylamino diphenylamine | 232 | $C_{16}H_{19}N_4O_2Cl$ | 57.40 | 5.68 | 16.74 | 10.60 | |
| | | | | 57.60 | 5.76 | 16.86 | 10.58 | |
| 40 | 2-ureido-4-hydroxy-3'-chloro-4'-N-methylamino diphenylamine | 213 | $C_{14}H_{15}N_4O_2Cl$ | 54.81 | 4.89 | 18.27 | 11.58 | |
| | | | | 54.42 | 5.05 | 18.54 | 11.59 | |
| 41 | semi-hydrate of 3,5-dimethyl-4-hydroxy-2-ureido-3'-chloro-4'-N-($\beta$-hydroxyethyl)amino diphenylamine | 170 | $C_{17}H_{21}N_4O_3Cl \cdot 0.5H_2O$ | 54.62 | 5.89 | 14.99 | 9.50 | |
| | | | | 54.48 | 5.70 | 15.19 | 9.36 | |
| 42 | 2-ureido-4-hydroxy-3'-chloro-4'-N-($\beta$-hydroxyethyl)amino diphenylamine | 183 | $C_{15}H_{17}N_4O_3Cl$ | 53.49 | 5.05 | 16.64 | | |
| | | | | 53.20 | 5.05 | 16.50 | | |
| 43 | 3-methyl-4-hydroxy-6-ureido-3'-chloro-4'-N-methylamino diphenylamine | 216 | $C_{15}H_{17}N_4O_2Cl$ | 56.16 | 5.30 | 17.47 | 11.07 | |
| | | | | 56.14 | 5.60 | 17.63 | 11.09 | |
| 44 | 3-methyl-4-hydroxy-6-ureido-3'-chloro-4'-N-($\beta$-hydroxyethyl)amino diphenylamine | 173 | $C_{16}H_{19}N_4O_3Cl$ | 54.78 | 5.42 | 15.97 | 10.13 | |
| | | | | 54.93 | 5.67 | 16.13 | 9.99 | |
| | | | | | | | 9.94 | |
| 45 | 3-methyl-4-hydroxy-6-carbamylmethylamino-3'-chloro-4'-N-methylamino diphenylamine | 218 | $C_{16}H_{19}N_4O_2Cl$ | 57.40 | 5.68 | 16.74 | 10.61 | |
| | | | | 57.08 | 5.90 | 17.00 | 10.34 | |
| 46 | 3-methyl-4-hydroxy-6-carbamylmethylamino-4'-N-methylamino diphenylamine | 197 | $C_{16}H_{20}N_4O_2$ | 63.98 | 6.71 | 18.65 | | |
| | | | | 63.84 | 6.92 | 18.86 | | |
| 47 | 3,6-dimethyl-4-hydroxy-3'-chloro-4'-N-methylamino diphenylamine | 95 | $C_{15}H_{17}Cl N_2O$ | 65.09 | 6.19 | 10.12 | | |
| | | | | 64.88 | 6.39 | 10.13 | | |
| 48 | 3,2'-dichloro-4-hydroxy-6-acetylamino-4'-N-methylamino diphenylamine | 190 | $C_{15}H_{15}N_3Cl_2O_2$ | 52.96 | 4.44 | 12.35 | 20.84 | |
| | | | | 53.05 | 4.71 | 12.20 | 20.62 | |
| 49 | 3-methoxy-4-hydroxy-6-amino-4'-N-methylamino diphenylamine | 157 | $C_{14}H_{17}N_3O_2$ | 64.86 | 6.56 | 16.22 | | |
| | | | | 64.99 | 6.80 | 16.31 | | |

(a) molecular weight, calculated
(b) molecular weight found by potentiometric determination in acetic acid with perchloric acid
(c) with decomposition

TABLE II

| | | | | | Ethanol (ml) | |
|---|---|---|---|---|---|---|
| No | BENZOQUINONEIMINE | quantity (g) | $Na_2S_2O_4 \cdot 2H_2O$ (g) | NaOH 1N (ml) | Temp. (° C) | (a) (b) |
| 1 | N[(4'-$\beta$-hydroxyethylamino-3'-methyl)phenyl]2-methyl-5-acetylamino benzoquinoneimine | 3.09 | 8 | 80 | 30 | |
| 2 | N-[(4'-acetylaminoethylamino-3'-methoxy)phenyl]2,6-dimethyl-3-amino benzoquinoneimine | 1 | 3 | 33 | 20 | 6 |
| 3 | N-[(4'-mesylaminoethylamino-3'-chloro)phenyl]2-methyl-5-acetylamino benzoquinoneimine | 1 | 3 | 33 | 20 | 6 |
| 4 | N-[(4'-ethylamino-2'-methyl)phenyl]3-ureido benzoquinoneimine | 1 | 4 | 35 | 25 | 12 |
| 5 | N-[(4'-mesylaminoethylamino-3'-methyl)phenyl]2,6-dimethyl-3-acetylamino benzoquinoneimine | 1 | 3 | 33 | 15 | 6 |
| 6 | N-[(4'-ethylamino-3'-methyl)phenyl]2,6-dimethyl-3-amino benzoquinoneimine | 1 | 6 | 50 | 40 | 10 |
| 7 | N-[(4'-ethylamino)phenyl]2-methyl-5-carbamylmethylamino benzoquinoneimine | 1 | 5 | 50 | 25 | 15 |
| 8 | N-[(4'-ethylamino)phenyl]2-methyl-5-acetylamino benzoquinoneimine | 1 | 6 | 50 | 25 | 15 |
| 9 | N-[(4'-methylamino)phenyl]2,6-dimethyl-3-acetylamino benzoquinoneimine | 1 | 3 | 33 | 20 | 12 |
| 10 | N-[(4'-methylamino-3'-methoxy)phenyl]2,6-dimethyl benzoquinoneimine | 1 | 3 | 33 | 30 | 6 |
| 11 | N-[(4'-$\beta$-hydroxyethylamino-3'-chloro)phenyl]3-chloro-6-acetylamino benzoquinoneimine | 1 | 3 | 33 | 15 | 6 |
| 12 | N-[(4'-ethylamino-3'-chloro)phenyl]2-methyl-5-acetylamino benzoquinoneimine | 1 | 3 | 33 | 25 | 10 |
| 13 | N-[(4'-$\beta$-hydroxyethylamino-3'-methoxy)phenyl]2,6-dimethyl-5-acetylamino benzoquinoneimine | 1 | 3 | 33 | 20 | 6 |
| 14 | N-[(4'-butylamino-3'-chloro)phenyl]3-acetylamino benzoquinoneimine | 1 | 4 | 80 | 25 | 10 |
| 15 | N-[(4'-$\beta$acetylaminoethylamino-3'-chloro)phenyl]3-methoxy benzoquinoneimine | 5.2 | 10 | 100 | 15 | 25 |
| 16 | N-[(4'-ethylamino-3'-methyl)phenyl]2-methoxy-5-acetylamino benzoquinoneimine | 3.27 | 6 | 60 | 20 | 20 |
| 17 | N-[(4'-methylamino-3'-methoxy)phenyl]2-methyl-5-carbethoxyamino benzoquinoneimine | 3.43 | 8 | 80 | 10 | 35 |
| 18 | N-[(4'-methylamino-2'-chloro)phenyl]2-methyl-5-$\beta$-hydroxy-ethylamino benzoquinoneimine | 3.2 | 6 | 60 | 25 | 20 |
| 19 | N-[(4'-methylamino)phenyl]2-methyl-5-amino benzoquinoneimine | 33 | 80 | 800 | 25 | 200 |
| 20 | N-[(4'-methylamino-2'-chloro)phenyl]2,6-dimethyl-3-acetylamino benzoquinoneimine | 39.8 | 70 | 720 | 20 | 250 |
| 21 | N-[(4'-methylamino-2'-methoxy)phenyl]2,6-di- | 22 | 40 | 400 | 15 | 150 |

TABLE II-continued

| I | II | | III | IV | V | VI | |
|---|---|---|---|---|---|---|---|
| | | | quantity | $Na_2S_2O_4 \cdot 2H_2O$ | NaOH 1N | Temp. | Ethanol (ml) |
| No | BENZOQUINONEIMINE | | (g) | (g) | (ml) | (°C) | (a) (b) |
| 48 | methyl-3-acetylamino benzoquinoneimine monohydrate of N-[(4'-methylamino-2'-chloro) phenyl]2-chloro-5-acetylamino benzoquinoneimine | | 3 | 10 | 120 | 5 | 20 |
| 49 | monohydrate of N-[(4'-methylamino)phenyl]2-methoxy-5-amino benzoquinoneimine | | 4.12 | 9 | 90 | 20 | |

TABLE III

| I | II | III | | IV | | V OXIDIZING AGENT | | | VI | VII | VIII |
|---|---|---|---|---|---|---|---|---|---|---|---|
| EX No | DYE Ex No | ADJUVANT nature | % | SOLVENT Nature | % | nature | ml | conc | pH | HAIR | COLOR |
| A1 | 8 | 0.05 AL 10.5 OE (1) | 5 | butyl glycol | 5 | $H_2O_2$ | 100 | 6% | 5.6 | D (a) | pearly light blue |
| A2 | 12 | 0.35 CMC (2) | 10 | | | $H_2O_2$ | 100 | 6% | 10 | " | pearly light mauve |
| A3 | 6 | 0.27 (NP 4 OE (3) | 5 | | | | | | | | |
| | | (NP 9 OE (3) | 5 | | | $H_2O_2$ | 25 | 6% | 6 | B95 (b) | slighty pink ash beige |
| A4 | 9 | 0.1 | | EMDE (4) | 10 | PSA | 100 | 1% | 8 | D (a) | pearly light blue |
| A5 | 14 | 0.05 | | isopropanol | 40 | $H_2O_2$ | 30 | 6% | 8 | " | pearly glycine |
| A6 | 2 | 0.60 | | ethanol | 20 | | | | 11 | " | deep violet |
| A7 | 3 | 0.40 DC (5) | 10 | | | $H_2O_2$ | 35 | 6% | 10.5 | " | very luminous mauve |
| A8 | 4 | 0.20 AL 10.5 OE (1) | 20 | | | PU | 100 | 10% | 6.1 | " | very luminous emerald green |
| A9 | 5 | 0.03 Al 10.5 OE (1) | 5 | | | $H_2O_2$ | 25 | 6% | 6.5 | " | very silvery light blue |
| A10 | 11 | 0.07 CMC (2) | 3.5 | isopropanol | 30 | $H_2O_2$ | 50 | 6% | 8.6 | " | pearly myosotis blue |
| A11 | 13 | 0.1 LSS 19 (6) EDTA (7) | 20 0.2 | | | $H_2O_2$ | 50 | 6% | 9.2 | D (a) | very pale emerald green |
| A12 | 7 | 0.2 oleyl-(O—CH₂—CH)₂OH \| CH₂OH oleyl-(O—CH₂—CH)₄OH \| CH₂OH | 5 5 | | | $H_2O_2$ | 50 | 6% | 9 | " | very luminous deep mauve |
| A13 | 1 | 0.41 | | ethanol | 35 | PU | 100 | 10% | 9 | " | silvery light blue gray |
| A14 | 11 C₁ C₂ C₃ C₄ | 0.20 LSS 19 (6) EDTA (7) 0.06 0.05 0.12 0.25 | 20 0.2 | | | $H_2O_2$ | 60 | 6% | 9.8 | B95 (b) | ash beige |
| A15 | 7 C₅ C₆ C₇ | 0.10 0.12 AL 10.5 OE (1) 0.04 0.05 | 5 | butylglycol | 5 | | | | 8 | D (a) | light copper chestnut |
| A16 | 9 | 3 DC (5) | 10 | | | $H_2O_2$ | 100 | 6% | 12 | B95 (b) | silvery lavender blue |
| A17 | 29 | 0.3 AL 10.5 OE (1) | 5 | butylglycol | 5 | | | | 7.5 | D (a) | purple violet |
| A18 | 32 | 2 LSS 19 (6) EDTA (7) | 20 0.2 | | | | | | 10.6 | " | sky blue |
| A19 | 20 | 0.2 AO 2 OE (8) AO 4 OE (8) | 3.7 5.5 | propyleneglycol | 7.4 | $H_2O_2$ | 30 | 6% | 9.5 | " | silvery light blue gray |
| A20 | 34 | 1 AcP (9) | 2.25 | ethanol | 25 | $H_2O_2$ | 60 | 6% | 10 | " | extremely rich violet blue |
| A21 | 37 | 1 AL 10.5 OE (1) | 5 | butylglycol | 5 | | | | 8 | " | silvery myosotis blue |
| A22 | 28 | 3 CMC (2) | 4.25 | ethanol | 15 | $H_2O_2$ | 25 | 6% | 10.5 | B95 (b) | purple |
| A23 | 40 | 1 LSS 19 (6) EDTA (7) | 20 0.2 | | | $H_2O_2$ | 40 | 6% | 10.5 | D (a) | silvery mauve gray |
| A24 | 31 | 3 CMC (2) | 4.5 | ethanol | 10 | | | | 5.5 | B95 (b) | deep ultramarine blue |
| A25 | 23 | 2 DC (5) | 8 | ethanol | 20 | $H_2O_2$ | 20 | 6% | 10 | D (a) | very luminous royal blue |
| A26 | 19 | 1.2 AO 2 OE (8) AO 4 OE (8) | 3.70 5.50 | propyleneglycol | 7.4 | PU | 1g | | 10.5 | B95 (b) | violet |
| A27 | 39 | 1.5 AL 10.5 OE (1) | 5 | | | | | | 6.5 | D (a) | silvery pale mauve |
| A28 | 41 | 2.5 NP 4 OE (3) NP 9 OE | 16 16 | ethanol | 20 | | | | 9.5 | " | pearly raw silk with mauve glints |
| A29 | 30 | 0.5 CMC (2) | 4 | ethanol | 20 | | | | 8 | " | very luminous violet blue |
| A30 | 21 | 0.65 AL 10.5 OE (1) | 20 | | | $H_2O_2$ | 25 | 6% | 8 | " | turquoise blue |
| A31 | 38 | 0.65 | | ethanol EMDE (4) | 20 | $H_2O_2$ | 25 | | 8.5 | " | silvery very light mauve |
| A32 | 33 | 3 DC (5) | 8 | ethanol | 20 | | | | 11 | " | silvery very light turquoise blue |
| A33 | 46 | 1.5 DC (5) | 7.5 | ethanol | 25 | $H_2O_2$ | 50 | 6% | 9 | B95 (b) | violet beige gray |
| A34 | 43 | 0.55 AO 20E (8) AO 40E (8) | 3.7 7.5 | propyleneglycol | 7.4 | $H_2O_2$ | 50 | 6% | 9 | D (a) | purple |
| A35 | 24 | 1.5 LSA (10) | 5 | | | | | | 8 | " | azure blue |
| A36 | 22 | 3 LSS 19 (6) EDTA (7) | 20 0.2 | | | PU | 1g | | 10 | " | silvery light gray |
| A37 | 44 | 1 | | ethanol EMDE (4) | 10 8 | $H_2O_2$ | 20 | 6% | 9.5 | D (a) | perme |
| A38 | 7 | 0.75 NP 40E (3) NP 90E (3) | 15 15 | ethanol | 25 | $H_2O_2$ | 25 | 6% | 9 | " | mauve |
| A39 | 42 | 2 AcP (9) | 3.6 | ethanol | 20 | $H_2O_2$ | 60 | 6% | 10.5 | B95 (b) | violet gray |
| A40 | 48 | 0.4 AcP (9) | 2.5 | ethanol | 25 | $H_2O_2$ | 60 | 6% | 10 | D (a) | very luminous glycine |

TABLE III-continued

| I | II | III | | IV | | V OXIDIZING AGENT | | | VI | VII | VIII |
|---|---|---|---|---|---|---|---|---|---|---|---|
| EX No | DYE Ex No | ADJUVANT nature | % | SOLVENT Nature | % | nature | ml | conc | pH | HAIR | COLOR |
| A41 | 49 | 0.75 AL 10.5 OE [1] | 20 | | | $H_2O_2$ | 50 | 6% | 10.5 | B95 [b] | mauve gray |

[a] D = bleached hair
[b] B95 = 95% naturally white hair
[1] AL 10.5OE = lauryl/alcohol oxyethylenated with 10.5 moles of ethylene oxide
[2] CMC = carboxymethyl cellulose
[3] NP × OE = nonylphenol polyoxyethylenated with x moles of ethylene oxide
[4] EMDE = monomethyl ether of diethylene glycol
[5] DC = diethanolamides of the fatty acids of copra
PS = ammonium persulfate
PU = urea peroxide
[6] LSS 19 = mixture constituted by 19% lauryl alcohol oxyethylenated with 2 moles of ethylene oxide and 81% of the sodium sulfate salt of this same oxyethylenated alcohol.
[7] EDTA = ethylenediamine tetracetic acid
$C_1$ = dihydrochloride of methoxyparaphenylene diamine
$C_4$ = paraminophenol
$C_2$ = hydroxyphenomorpholine
$C_3$ = 2,4-diaminoanisole dihydrochloride
$C_5$ = 3-methoxy-4,6-diamino-4'-hydroxy-diphenylamine dihydrochloride
$C_6$ = 2,6-diamino-4-N,N-diethylaminophenol,trihydrochloride
$C_7$ = nitrometaphenylenediamine
[8] AO × OE = oleyl alcohol oxyethylenated with x moles of ethylene oxide
[9] AcP = polyacrylic acid (MW = 2 to 3 million)
[10] L.S.A. = lauryl ammonium sulfate

TABLE IV

| I | II | | III | | | | IV | | V | VI | VII |
|---|---|---|---|---|---|---|---|---|---|---|---|
| Ex No | DYE Ex No | wt% | POLYMER Name | M.W. | Cps | % | ALCOHOL Name | % | pH | HAIR | COLOR |
| B1 | 2 | 0.50 | VP 30/VA 70 | 160,000 | | 3 | ethanol | 50 | 10.5 | B95 (b) | violet light chestnut |
|  | 12 | 0.40 | | | | | | | | | |
|  | 08 | 0.10 | | | | | | | | | |
|  | 09 | 0.20 | | | | | | | | | |
| B2 | 10 | 0.53 | PVP | 40,000 | | 2 | isopropanol | 25 | 9.7 | D (a) | deep violet |
| B3 | 10 | 0.05 | VP 30/VA70 | 160,000 | | 2 | ethanol | 40 | 9.5 | D (a) | very luminous pearly blue |
| B4 | 10 | 0.07 | VA 90/CA10 | 45,000-50,000 | | 1 | ethanol | 40 | 10 | B95 (b) | pink beige |
|  | 4 | 0.22 | | | | | | | | | |
|  | C10 | 0.22 | | | | | | | | | |
|  | C9 | 0.09 | | | | | | | | | |
| B5 | 15 | 0.15 | VA90/CA10 | 45,000-50,000 | | 2 | ethanol | 50 | 10 | D (a) | pearly mauve |
| B6 | 16 | 0.60 | PVP | 40,000 | | 2 | isopropanol | 25 | 7 | " | very luminous periwinkle blue |
| B7 | 17 | 0.45 | Gafquat 734 | 100,000 | | 2 | isopropanol | 20 | 7 | " | light turquoise blue |
| B8 | 18 | 0.25 | VA90/CA10 | 45,000-50,000 | | 1 | ethanol | 36 | 6.5 | " | silvery glycine |
| B9 | 18 | 0.40 | VP60/VA40 | | *3.3 to 4 | 2 | isopropanol | 35 | 4.5 | B95 (b) | dark violet |
| B10 | 17 | 0.40 | VP60/VA40 | | 3.3 to | 2 | isopropanol | 35 | 8 | D (a) | violet |
| B11 | 15 | 0.30 | PVP | 40,000 | | 2 | isopropanol | 25 | 8 | " | very luminous mauve |
| B12 | 45 | 0.30 | VA80.5/AS15/AOA4.5 | | 4.5 | 2.5 | ethanol | 50 | 7.5 | D (a) | salmon |
| B13 | 36 | 0.25 | VP 30/VA70 | 160,000 | | 2 | ethanol | 40 | 4 | " | silvery light mauve gray |
| B14 | 18 | 0.40 | Gantrez ES435 | | 0.962 | 1 | ethanol | 45 | 9 | " | pearly parme |
| B15 | 47 | 0.3 | VP60/VA40 | | 3.5 | 2 | isopropanol | 35 | 7 | D (a) | pearly light raw silk with mauve glints |

*viscosity determined starting with a 5% solution in ethanol at a temperature of 25° C.

In Table IV, above:
C8 = N-[(4'-hydroxy)phenyl]-2,6-dimethyl benzoquinoneimine;
C9 = nitroparaphenylene diamine
C10 = 1-γ-amino propylamino anthraquinone
VP30/VA70 = copolymer of 30% vinylpyrrolidone and 70% vinyl acetate sold under the mark PVP/VA E335;
VP60/VA40 = copolymer of 60% vinylpyrrolidone and 40% vinyl acetate sold under the mark PVP/VA S 630;
VA90/CA10 = copolymer of 90% vinyl acetate and 10% crotonic acid;
Gafquat 734 = quaternary copolymer of polyvinylpyrrolidone;
VA80.5/AS15/AOAA4.5 = copolymer of 80.5% vinyl acetate, 15% allyl stearate and 4.5% allyloxyacetic acid; and Gantrez ES 435 = monobutyl ester of the copolymer of maleic anhydride and methyl vinyl ether.

What is claimed is:

1. A composition for coloring keratinic fibers comprising an aqueous or hydroalcoholic solution of at least one diphenylamine of the formula

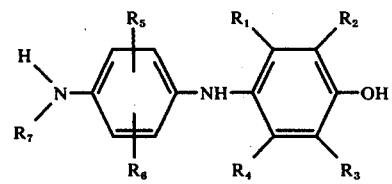

wherein $R_1$ and $R_4$ each independently represent a member selected from the group consisting of hydrogen, halogen, lower alkyl having 1-6 carbon atoms, lower alkoxy having 1–6 carbon atoms, amino, N-lower alkyl amino wherein the alkyl moiety has 1–6 carbon atoms, N-lower hydroxy alkyl amino wherein the alkyl moiety has 1–6 carbon atoms, N-lower carbamylalkylamino wherein the alkyl moiety has 1–6 carbon atoms, acetylamino, ureido and carbalkoxyamino wherein the alkoxy moiety has 1–6 carbon atoms;

$R_2$ and $R_3$ each independently represent a member selected from the group consisting of hydrogen, lower alkyl having 1–6 carbon atoms, lower alkoxy having 1–6 carbon atoms, acelyamino and ureido;

$R_5$ and $R_6$ each independently represent a member selected from the group consisting of hydrogen, halogen, lower alkyl having 1–6 carbon atoms and lower alkoxy having 1–6 carbon atoms with the proviso that when both $R_5$ and $R_6$ are other than hydrogen at least one of $R_5$ and $R_6$ occupies a position meta to $-NHR_7$; and $R_7$ represents a member selected from the group consisting of alkyl having 1–6 carbon atoms, hydroxyalkyl having 1–6 carbon atoms, amino alkyl having 1–6 carbon atoms, acetylamino alkyl wherein the alkyl moiety has 1–6 carbon atoms and mesylamino alkyl having 1–6 carbon atoms, said diphenylamine being present in an amount effective to color said keratinic fibers.

2. The composition of claim 1 wherein said diphenylamine is present in an amount of about 0.002 to 3 percent by weight of said composition.

3. The composition of claim 1 having a pH between about 5.5 – 12.

4. The composition of claim 1 which also includes direct hair dye.

5. The composition of claim 1 which also includes a member selected from the group consisting of an oxidation dye and a coupler.

6. The composition of claim 5 wherein said oxidation dye is selected from the group consisting of orthophenylenediamine, paraphenylene diamine, orthoaminophenol and paraaminophenol.

7. The composition of claim 5 wherein said coupler is selected from the group consisting of metadiamine, metaaminophenol, metaacetylaminophenol and metadiphenol.

8. The composition of claim 1 which also includes a dye selected from the group consisting of a nitrobenzene dye, an anthraquinone dye, and an indophenol.

9. The composition of claim 1 which is a hydroalcoholic solution of said diphenylamine and which also includes at least one cosmetic film-forming resin.

10. The composition of claim 9 wherein said hydroalcoholic solution is an aqueous solution of a low molecular weight alcohol.

11. The composition of claim 10 wherein said alcohol is selected from the group consisting of ethanol and isopropanol.

12. The composition of claim 10 wherein said alcohol is present in an amount of about 20–70 weight percent.

13. The composition of claim 9 wherein said cosmetic film-forming resin is present in an amount of 1–3 weight percent.

14. The composition of claim 9 wherein said cosmetic film-forming resin is selected from the group consisting of polyvinylpyrrolidone, a copolymer of vinylpyrrolidone and vinyl acetate, a copolymer of vinyl acetate and crotonic acid, a copolymer of maleic anhydride and butyl vinyl ether, a terpolymer of methyl methacrylate, stearyl methacrylate and dimethylaminoethyl methacrylate and a terpolymer of vinyl acetate, allyl acetate and allyloxy acetic acid.

15. The composition of claim 1 in the form of a cream or a gel.

16. The composition of claim 1 which also includes a glycol.

17. The composition of claim 1 which also includes a wetting agent.

18. The composition of claim 1 which also includes a dispersing agent.

19. A process for dyeing keratinic fibers comprising impregnating said fibers to be dyed with the composition of claim 1 in an amount effective to dye said fibers, permitting said composition to remain in contact with said fibers for a period ranging from about 5 to 30 minutes, rinsing said fibers and drying said fibers.

20. The process of claim 19 wherein said fibers are living human hair and said hair after rinsing is shampooed prior to drying the same.

21. A process for coloring human hair comprising applying to previously washed and rinsed hair the composition of claim 9 in an amount effective to color said hair.

* * * * *

UNITED STATES PATENT AND TRADEMARK OFFICE
CERTIFICATE OF CORRECTION

PATENT NO. : 4,008,043

DATED : February 15, 1977

INVENTOR(S) : Gregoire Kalopissis, Andree Bugaut and Francoise Estradier

It is certified that error appears in the above-identified patent and that said Letters Patent are hereby corrected as shown below:

Col. 23, line 10, before "lower alkyl" insert

--halogen, --.

line 11, change "acelyamino" to --acetylamino--.

Signed and Sealed this

Thirtieth Day of October 1979

[SEAL]

*Attest:*

RUTH C. MASON
*Attesting Officer*

LUTRELLE F. PARKER
*Acting Commissioner of Patents and Trademarks*